United States Patent
Lazik et al.

(10) Patent No.: US 9,010,174 B2
(45) Date of Patent: Apr. 21, 2015

(54) METHOD AND DEVICE FOR THE MEMBRANE-BASED ANALYSIS OF GAS COMPONENTS

(75) Inventors: Detlef Lazik, Salzatal (DE); Dieter Lazik, Beetzsee (DE); Wolfgang Rehak, Berlin (DE)

(73) Assignee: Membranbasierte Gassensoren UG (Haftungsbeschraenkt)—Megasen, Potsdam (DE)

( * ) Notice: Subject to any disclaimer, the term of this patent is extended or adjusted under 35 U.S.C. 154(b) by 402 days.

(21) Appl. No.: 13/518,649

(22) PCT Filed: Dec. 16, 2010

(86) PCT No.: PCT/EP2010/069884
§ 371 (c)(1), (2), (4) Date: Aug. 30, 2012

(87) PCT Pub. No.: WO2011/076659
PCT Pub. Date: Jun. 30, 2011

(65) Prior Publication Data
US 2012/0318043 A1    Dec. 20, 2012

(30) Foreign Application Priority Data
Dec. 23, 2009 (DE) .......................... 10 2009 060 583

(51) Int. Cl.
  *G01N 7/10* (2006.01)
(52) U.S. Cl.
  CPC .................................... *G01N 7/10* (2013.01)
(58) Field of Classification Search
  CPC .......................................................... G01N 7/10
  USPC .............................................. 73/31.04, 31.07
  See application file for complete search history.

(56) References Cited

U.S. PATENT DOCUMENTS

| | | | | |
|---|---|---|---|---|
| 2,811,037 A * | 10/1957 | Beard | ........................... | 73/31.04 |
| 2,909,919 A * | 10/1959 | Myer | ........................... | 73/31.04 |
| 4,208,902 A * | 6/1980 | Kim et al. | ................... | 73/31.07 |
| 4,598,576 A * | 7/1986 | Goldsmith et al. | .......... | 73/31.07 |
| 4,858,461 A * | 8/1989 | Steinle et al. | ................ | 73/31.04 |

FOREIGN PATENT DOCUMENTS

| | | | |
|---|---|---|---|
| DE | 4316196 A1 | 10/1993 | |
| DE | 19925842 A1 | 12/2000 | |
| DE | 10220944 C1 | 12/2003 | |
| EP | 1359414 A2 * | 11/2003 | ............. G01N 33/00 |

OTHER PUBLICATIONS

Machine Translation of EP 1359414.*
Lazik D et al; "A new method for membrane-based gas measurements," Sensors and Actuators A, Elsevier Sequoia S.A., Lausanne, CH, vol. 117, No. 2, Jan. 14, 2005, pp. 241-251.
International Search Report for PCT/EP2010/069884 dated Oct. 18, 2011.

* cited by examiner

*Primary Examiner* — Peter Macchiarolo
*Assistant Examiner* — Nathaniel Kolb
(74) *Attorney, Agent, or Firm* — Heslin Rothenberg Farley & Mesiti P.C.

(57) ABSTRACT

A method and a device for the analysis of gas components of a matrix employ two sensors, which each comprise a cavity enclosed by a membrane. Both membranes, each on one side of the matrix and on the other side, are exposed to a purge gas and subsequently, the timeline of the differential pressure $\Delta p_s$ starting at a start time $t_A$ is measured, which is created between the sensors as a consequence of permeation of gas components of the matrix and/or the purge gas through both membranes. From the timeline, a point of time $t_E$ is determined, at which the measured differential pressure equals the differential pressure at the point of time $t_A$, whereby the gas component of the matrix, which is different from the purge gas, and its genesis is determined from the time difference $\Delta t = t_E - t_A$.

Figure 1:
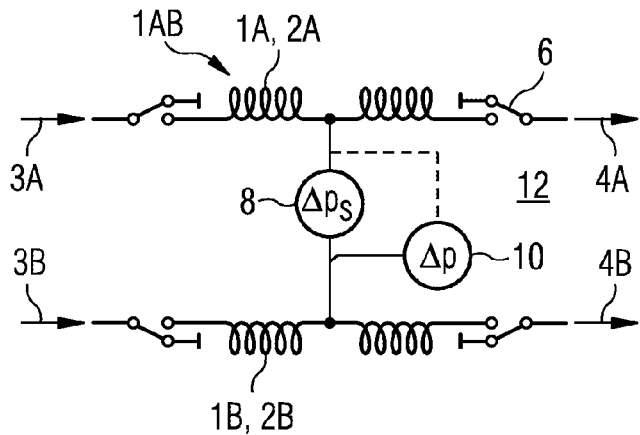

15 Claims, 2 Drawing Sheets

METHOD AND DEVICE FOR THE MEMBRANE-BASED ANALYSIS OF GAS COMPONENTS

CROSS REFERENCE TO RELATED APPLICATIONS

This application is a national stage filing under section 371 of International Application No. PCT/EP2010/069884 filed on Dec. 16, 2010, and published in German on Jun. 30, 2011 as WO 2011/076659 A2 and claims priority of German application No. 10 2009 060 583.5 filed on Dec. 23, 2009, the entire disclosure of these applications being hereby incorporated herein by reference.

BACKGROUND ART

The invention relates to a method for the identification of gas components in various phases and mixtures of phases of an examination area, in which the gas components can be present dissolved or in gaseous form. The invention also relates to devices for the realization of this method.

For the purpose of a qualitative and quantitative determination of components of a gas in the examination area, that in the following is designated as matrix and can occur as a phase in itself and dissolved in other phases, various methods are known, which make use of the selective permeation of gas components through membranes. Conditions for the quantitative analysis of the concentration of selected known gas components, which are often of interest from a practical point of view, are that the change in the composition of the matrix is caused by changes in concentration of the examined gas components.

Therefore, DE 199 25 842 A1 describes a method, in which the concentration or the partial pressure of gas component contained by a fluid is determined by how quickly the pressure changes.

According to various applications, sensors of different geometries are available, which can be brought into contact with the matrix that is to be examined by minimally interfering with the processes run within the examination area. Thus, a tube-shaped geometry permits the averaging of the concentration along the observed line of laying out in the examination area. According to DE 199 25 842 A1, such a sensor system including a suitable reference sensor system can be installed in a fixed manner within the examination area for the in-situ measurement and does not require any further maintenance.

For membrane-based analysis methods, the used membrane is in contact with the phase containing the matrix on one side, while on the other side a cavity, at least partly enclosed by the membrane, is filled with a gas of known composition. A difference in concentration of gas components on both sides of the membrane causes a diffusive flow of gas molecules through the membrane, and in this way, leads to a change of the partial pressures within the cavity, which can be measured as a change in pressure or volume of the gas phases in the cavity.

The cavity enclosed at least partly by a membrane, which is provided with suitable sensors for measuring pressure or volume or with a measurement value dependent on this measurement, is called a measurement chamber. The measurement chamber in its construction and various components is adapted to the method applied. In this way, the measurement chamber can have if necessary a controllable closing system and a supporting body for the mechanical stabilisation against possible differences in pressure on either side of the membrane. Also, a radial symmetry of the membrane geometry can be used for securing the measurement chamber geometry, whereby the measurement chamber is arranged both on inside and the outside of the radial symmetrical membrane.

Measurement chamber and membrane form a measurement sensor also simply designated as sensor, which if required can be combined with a reference sensor. The latter can have a structure that is analogue to the measurement sensor. A sensor possesses a geometry factor, from which physically relevant geometrical characteristics of the measurement chamber and membrane can be derived as well as a membrane-dependent gas selectivity, which determines how the permeation coefficients of the membrane for the gas components differ from each other. Permeation here is understood as the combination of solution and diffusion of a gas component in the membrane. So far, membranes, which exclusively can be permeated for a gas component, are not known. However, various membranes are distinguished by different sequences of selectivity for individual gas components of the matrix.

The measurement device as described in DE 102 20 944 A1 realizes a spatial segregation between sampling using a sampling element (phase separator) permeable to gases, which is in contact with the materials of the area to be examined on one side, and the sensor system. The latter is based on the sensor system as described in DE 199 25 842 A1. Sensor and sampling element are connected to each other through a circular line permeable to gases. The gas within the circular line can be moved through the circular line, sampling element and sensor permanently or event-initiated using a pump. The change of the pressure within the closed system as a consequence of adjusting the equilibrium of the gas composite within the measurement device through the matrix can serve as an initiating event. Besides the convective conditioning of the measurement chamber via a purge gas, its diffusive conditioning is described via the gas phase circulating through the circular line. For increasing the sensitivity, measurement chambers identical in construction are realized in a differential gas sensor on both sides of the membrane, and the pressure-time behaviour between both measurements chambers are identified using the differential pressure established between both measurement chambers.

The initial state of the measurement, designated by a known gas composite within the measurement chamber and a defined relation between gas and the matrix, can be adjusted to be convective (DE 199 25 842 A1) through the closing system of the measurement chamber, or can be diffusive through the membrane (DE 102 20 944 A1), and is called conditioning.

Under certain conditions, the selectivity of the membrane dependent on a gas component out of equilibrium causes different timelines for re-establishing of the equilibriums on both sides of the membrane. In this way, the measured pressure-time or volume-time curves can be referred back to the original differences in concentrations of one or more gas components. For the given matrix, a component-dependent calibration can be provided for the used sensor in this regard.

If one calculates the different pressure-time curves, which were identified behind membranes of different selectivities, in a system of equations and considers the known initial gas composition in the measurement chambers, it will lead to the theoretically possible and complete analysis of the matrix.

If the matrix composite is of a complex composition, such an analysis requires a high instrumental and technical effort from a practical point of view. Further, there may not be a sufficient amount of membrane materials with sufficient selectivity.

However, the analysis of the matrix itself is often not needed but the analysis of the concentration of a gas component in the matrix is. For instance, this is the concentration or the partial pressure of a qualitatively known gas component, which occurs in the matrix through leakage from a technical device. In an otherwise unamended matrix, this is only possible via a sensor according to DE 199 25 842 A1. Therefore, two different selective sensors are necessary for verification of the concentration for two qualitatively known gas components, which can change independently from each other in the matrix, etc.

Such gas sensors can be used in very different areas, for which the concentrations of the gas components can change. The changes in concentration can have various origins, e.g. transport of material or chemical processes. In this respect, such gas sensors, e.g. used for the monitoring of gas components in waters, soil and rocks, where one must take into consideration biogeochemical processes, or for the monitoring and control of technical devices, disposal sites, reconstruction of contaminated sites, etc.

In particular in regards to gases relevant to the climate, e.g. carbon dioxide ($CO_2$) in relation to the Carbon-Capture-and-Storage-Technology (CCS), monitoring systems, which can be used in a representative and cost efficient manner in-situ are of interest.

In this and similarly in further embodiments, a differentiation of a gas component however can be required in regards to its origin (genesis). Using the example of $CO_2$, it is to be distinguished that $CO_2$ can not only escape from technical or geotechnical devices, e.g. pipelines, grouting drillings or reservoir rock, but also in the relevant monitoring area, e.g. created in soil through metabolic processes. In the first instance, the source is external; in the second instance, it is an internal reaction or soil respiration. A security system should be able to distinguish CCS—$CO_2$ from $CO_2$ as a consequence of soil respiration for such applications. The monitoring of external sources in the monitoring area soil can also be necessary for ascending $CO_2$ as a consequence of smoldering fires or volcanic activity.

For a so called genetic, i.e. origin-based analysis, effortful methods are used to this point, which, for instance, make use of differences in isotope signatures of the various gas sources, which is done with high technical, financial and staff effort. Further, the differences in isotope signature of the gas sources are in some cases not distinct enough, not temporally constant or are subject to changes on their way from source to examination area.

BRIEF SUMMARY OF INVENTION

The invention therefore is meant to present a method and a device that can be used for this method, which enable a quantitative change of the concentration of a gas component with its qualitatively explicit identification in a given matrix, and in this way allow its genetic differentiation.

This solution of the task according to the invention takes place via the analysis of the differential pressure-time curve $\Delta p_s(t)$ between the measurement chambers of two sensors coordinated specifically in their geometry and selectivity, which both have a cavity enclosed by a membrane and simultaneously are exposed to the matrix that is to be examined.

The coordination of the geometry and selectivity of the pair of sensors takes place in a way, that it results in different timelines of the permeation of the gas components for the matrix that is to be examined in or from the measurement chambers for given conditions.

The measurement takes place starting from an initial state that can be replicated. This state alternatively can be achieved through adjusting a thermodynamic equilibrium, for which no diffusive gas flows can be registered anymore following the completion of the conditioning, or through adjusting a dynamic equilibrium, for which stationary diffusive gas flows are present following the completion of the conditioning.

For adjusting the thermodynamic equilibrium between the gases on both sides of the membrane, a simply constructed passive, i.e. diffusively purged pair of sensors can be used. Such a pair of sensors requires no devices for the opening or closing of the measurement chambers. The starting point $t_A$ of the measurement follows a process-driven diffusive deviation from the equilibrium as a consequence of the change of concentration of a gas component in the matrix. It can be defined through the beginning of the differential pressure between the measurement chambers or pressure in the measurement chamber changing.

For adjusting the dynamic equilibrium, the measurement chambers are purged using a gas of a known composite and are subsequently closed, for which actuatory components for opening or closing of the measurement chambers such as valves are provided. During the conditioning, the measurement chambers are connected with a purge gas supply system. The starting point $t_A$ of the measurement in this case is defined through the point of time, at which the measurement chambers are closed preferably in addition to a definable offset.

Originating from a state of equilibrium, the starting point $t_A$ can be selected, so that the differential pressure $\Delta p_s$ between the measurement chambers is approximately zero. Alternatively, other replicable points of time, e.g. of extreme values, turning points, etc. on the pressure-time curve of the differential pressure can be chosen for both versions of the method.

Because of the permeation processes on both membranes that differ from each other, the following pressure process in the measurement chambers develops differently after the starting point $t_A$. The suitable combination of sensors leads to both pressure-time curves separating themselves far from the equilibrium that is re-established for longer periods, whereby the differential pressure $\Delta p_s(t)$ at the point of time $t=t_E$ again reaches the value assumed at the starting point, e.g. approximately zero. This point of time $t_E$ shall be called end point for the purpose of distinction, whereby the designation "end" merely refers to the point of time, which together with the starting point is used for determining the characteristic time difference $\Delta t = t_E - t_A$, and which in no way is related to the course of the measurement. Further, the pressure processes converge for a comparably significant amount of time with a re-establishing of the equilibrium against each other.

Analogue to the choice of the starting point $t_A$, the choice of the end point $t_E$ can be specified for this process according to the pressure-time curve realized under respective measurement conditions using a characteristic and replicable point of time.

Now it was found that the time difference $\Delta t = t_E - t_A$ for given measurement conditions and matrix is characteristic for the gas component, whose concentration has changed in the matrix, however which is independent from the extent of the change as the time difference $\Delta t$ remains completely constant across the theoretically possible mixing range.

For the specific realization of the method, it was found that the stated characteristic points of time of the differential pressure remain the same in regards to their characteristics independent of the method procedure. This enables both a process-driven and thus, event-orientated reaction of the measurement system, which is based on the non-stationary gas diffusion that originates when the thermodynamic equilibrium is disturbed, and an observer-driven operating, for instance, through making use of the dynamic equilibrium as the starting point of the measurement.

Surprisingly, it was found further that a reaction also occurring in the matrix, following which the concentration of two gas components change through a linked defined reaction, can be identified also through a characteristic time difference $\Delta t_0$, the reaction-matrix time, which in turn differs from the time difference $\Delta t_{mix}$, which results from the mere change of an involved gas component and which is also called the mixture-matrix time. In this way, equimolar reactions between two gas components A and B of the matrix, e.g. the transformation of A to B, show in turn an independence of the time difference $\Delta t_0$ to the concentration and thus, an independence, for instance, to the intensity of the reaction. Using the above presented example of soil respiration, component A would be oxygen and component B would be carbon dioxide.

If a further process besides this internal reaction, at which merely A and B is influenced, causes the involvement of A and B from an external source into the matrix, the added gas component changes the partial pressure of all of the gas components already present in the matrix. The latter mixing process is consistent with the already above presented change of the concentration of a gas component in the matrix. If the relative proportion of the added gas component related to the total concentration increases, the measurable time difference can shift from the time difference characterized by the reaction to the one for a pure mixing process of the gas component with the matrix. At this point, it shall be specified that the designation $\Delta t$ is always used without any addition if the time difference can be determined both from the reaction of at least two gas components in the matrix and the adding of at least one components in the matrix.

Under given measurement conditions for an initially present matrix composite, for instance the shifting of the time difference $\Delta t$ from a constant, e.g. of an equimolar reaction is solely determined by the composite intensity of a gas component originating from an external source.

The time difference $\Delta t$ per se and its change is in this way a measure independent from an internally operating, differently intensive reaction for the genetic differentiation between the proportion of the gas components made of reaction and mixing. It can be identified and experimentally determined through a mathematical simulation, and can be provided for the calibration of the measurement.

The geometry and selectivity of the pair of sensors can be chosen depending on various parameters. In particular, the components of the matrix have an influence on the choice of materials. However, also size and make of the examination area and of the dynamics of processes running within that is to be dissolved determine the characteristics of the sensor system. Further, the physical or chemical environmental conditions can require certain characteristics from the sensors. For this purpose, a wide palette of different membrane and measurement chamber materials are available.

According to one embodiment of the invention, the measurement device comprises besides the pair of sensors, which is exposed to the matrix, another pair of sensors advantageously identical in construction as a reference. This reference however is exposed on both sides of the membrane to the same gas. Also in the reference, the development over time of the differential pressure $\Delta p_r(t)$ is determined, so that the timeline of method—and environmental-based influences on the measurement system can be presented. The timeline of the reference differential pressure $\Delta p_r(t)$ is designated as baseline in the following. By relating the differential pressure of the pair of sensors to the one of the reference, methodological and environmental influences can be eliminated from the identification of $\Delta t_0$, $\Delta t_{mix}$ and $\Delta t$.

Reaching the points of time $t_A$ and $t_E$ takes place according to description as above because of the closed volumes of the measurement chambers in an isochoric manner. Alternatively, the points of time $t_A$ and $t_E$ can be defined in an isobar way for the pair of sensors or reference sensors in an analogue manner through the measurement of the differential volumes and re-establishment of a defined volume or volume flow. With identifying the characteristic points of time and time differences through this measurement, the described evaluation can also be used for the isobar realization of the method.

As purge gas and for the calibration of the built-in sensor system, different purge gases are used depending on the matrix and the gas components to be examined.

BRIEF DESCRIPTION OF DRAWING FIGURES

Figure 2:
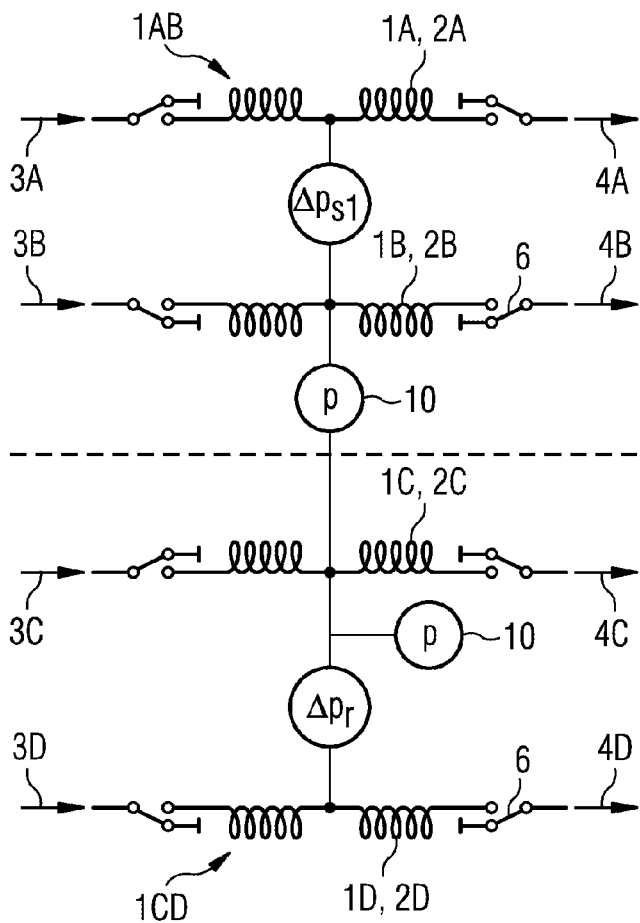
Figure 3:
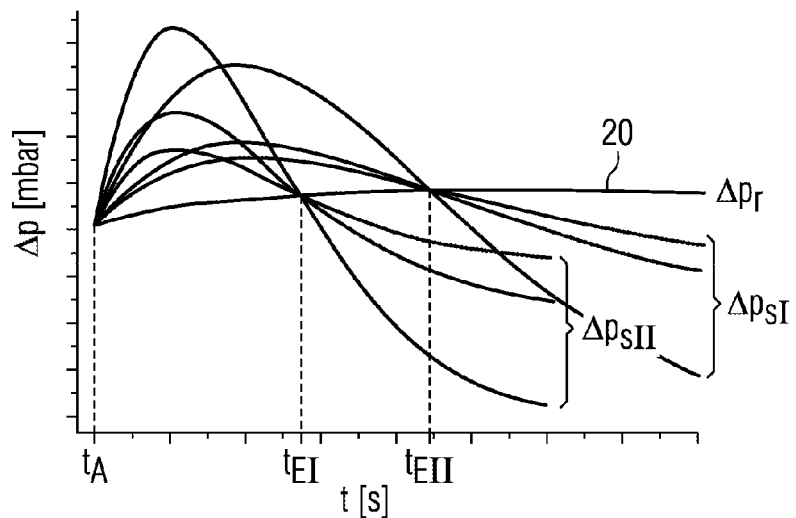

The invention shall be described more in detail in the following using an embodiment. The associated drawings show:

FIG. 1 a measurement device with a pair of tube-shaped sensors,

FIG. 2 a measurement device with reference-based sensors,

FIG. 3 the course of the differential pressure $\Delta p_s(t)$ for two different gases above the baseline determined through the reference measurement, and measured out of the dynamic equilibrium, FIG. 4 the independence of the concentration of distinct time differences $\Delta t$ for gas components added to the matrix or subsequently formed an internal reaction in the matrix, determined through measurement out of a thermodynamic equilibrium.

DETAILED DESCRTIPTION

The method of measurement as well as the measurement system used for this method are described using two connected sensors. Method and system however can also be applied to several sensors with different characteristics, which are connected and operated in an analogue manner.

The description of the invention shall be done without any restrictions on a general application of the gas analysis in the water-saturated soil. The matrix is present as a gas in equilibrium in relation to the atmosphere, dissolved in ground water and adsorbed or absorbed on and in solid material. To simplify matters, local solution and sorption equilibriums are assumed for the gas components of the matrix between the different phases.

FIG. 1 presents the principal structure of a measurement device, which can be used for the qualitative and quantitative analysis of individual gases and for the genetic gas differentiation of gas components in a matrix 12.

The measurement device comprises two sensors 1A, 1B, which are realized as tube-shaped in the presented embodiment, but can also have other shapes. Both sensors 1A, 1B are arranged simultaneously and adjacent to each other in the gas composite to be examined, i.e. in the matrix 12, so that both membranes of the pair of sensors 1AB are completely enclosed by the matrix 12.

A sensor 1A, 1B is essentially made up of a cavity with a measurement chamber volume V1, V2, whose walls completely, as in the depicted tube-shape, or at least in parts are made up of a membrane 2A, 2B permeable to gases.

Both tube-shaped sensors 1A, 1B have each a purge gas inlet 3A, 3B on one end as well as a purge gas outlet 4A, 4B on the other end. Purge gas in- and outlets 3A, 3B, 4A, 4B can be closed through valves 6.

The differential pressure $\Delta p_s$, which is established between both sensors 1A, 1B, is measured using a differential pressure sensor 8. Additionally, the pressure is measured using a pressure sensor 10 in at least one of the sensors 1A, 1B (dotted line), preferably a relative pressure sensor.

Such a or a similar measurement device allows a neglected interaction between the environment to be monitored and sensor through the below described realizations of the method as a consequence of reducing diffusive processes. They permit a lost sensor installation in the examination area and a certain separation between examination and control area, which can only be overcome diffusively through available gases. Further, necessary operations such as cleaning, testing of functionality, calibration take place on the sensor system, e.g. which are in the soil, only out of the inside of the measurement chamber.

A method for the analysis of individual gases, which makes use of the adjustment of the dynamic equilibrium at the starting point, and subsequently is designated as active measurement, following procedural steps comprising:

First of all, a convective conditioning of the measurement device takes place, by having purge gas, in this embodiment air, flow through both sensors 1A, 1B with opened valves 6. As a result of this conditioning, both membranes of the pair of sensors 1AB are exposed to the matrix 12 to be examined on their outside and to the purge gas on their inside.

At the point of time, the pair of sensors 1AB are closed by the valves 6, so that the differential pressure equals zero at the starting point. Through closing the sensors 1A, 1B, the measurement is started. Commencing from the starting point $t_A$, the timeline of the differential pressure $\Delta p_s$ (FIG. 3) using the differential pressure sensor 8 and the timeline of the pressure in sensor 1B using the pressure sensor 10 are measured.

From the recorded timeline $\Delta p_s(t)$, the point of time is identified, at which the differential pressure $\Delta p_s$ of the pair of sensors, which is exposed to the matrix 12, has reached the same value as the differential pressure $\Delta p_r$ of the reference measurement. This end point $t_E$ presents the equalization of pressure between both membranes of the pair of sensors 1AB. Knowing $t_E$, the characteristic time difference $\Delta t = t_E - t_A$ can be calculated.

Figure 4:
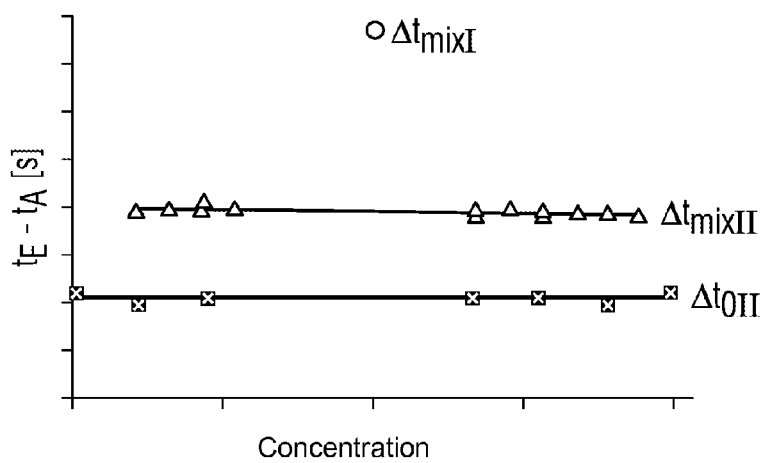

By comparing the reference timelines through mathematical simulations or through calibrating the measurement system in relation to the gas components of interest, the wanted type of gas component of the matrix 12 is identified using the calculated characteristic time difference $\Delta t = t_E - t_A$ (FIG. 4). Using the same characteristic time difference $\Delta t$, one can imply the genesis of the gas component by taking into consideration the different reaction- and composition-matrix times $\Delta t_0$ and $\Delta t_{mix}$ (FIG. 4) known for this type.

In addition to the described course of the method, the concentration and its change can be identified in a quantitative manner for the qualitatively determined gas component from the time-dependent pressure measurement with the pressure sensor 10 or from the pressure-time curve of the differential pressure $\Delta p_s(t)$. For the realization of the method, DE 199 25 842 A1 is pointed out, to which it is explicitly referred here. For the combination of the qualitative and the quantitative analysis, the differences of the pressure-time curves from the qualitative analysis can efficiently serve the expansion of the measurement areas, by basing it on a component-dependent calibration to determine the concentration.

For consideration of such characteristics of the sensors and such local, physically relevant characteristics of the measurement environment for determining the time difference $\Delta t = t_E - t_A$, whose difference between both sensors can influence the differential pressure $\Delta p_s(t)$, the measurement sequence of the above presented steps 1 and 2 can be carried out in a reference measurement system, in which the sensors are surrounded by the purge gas used in the chambers. In this way, a so called baseline 20 (FIG. 3) is identified, which alternatively is used for determining the end point $t_E$, by defining $t_E$ as the point of time at which the differential pressure $\Delta p_s$ crosses the baseline 20 instead of the abscissa of the $\Delta p$-t-graph. The differential pressure, which is identified in the reference measurement system shall be called reference differential pressure $\Delta p_r$.

FIG. 2 presents a measurement device, in which a drift correction of the differential pressure signal $\Delta p_s$ in relation to the reference differential pressure $\Delta p_r$ is metrological realized. A pair of reference sensors 1CD identical in construction with a pair of sensors 1AB, as described in FIG. 1, is used as a reference by exposing its membrane 2C, 2D on both sides to the purge gas. Sensors, membranes, purge gas inlet and outlet of the reference system are designated with the letters C and D.

The differential pressure $\Delta p_s$ is identified in the embodiment according to FIG. 2 taking into consideration the reference differential pressure, which is measured between both of its sensors 1C, 1D in the reference system. It is concluded from the following calculation:

$$\Delta p_s = \Delta p_{sI} - \Delta p_r,$$

whereby $\Delta p_{sI}$ in this case is the differential pressure, which is actually measured between both of the sensors 1A, 1B exposed to the matrix 12. Through $\Delta p_s$ identified in this manner, the end point $t_E$, the time difference $\Delta t = t_E - t_A$ as well as the reaction—and mixture—matrix time $\Delta t_0$ and $\Delta t_{mix}$ can be determined as described above in FIG. 1. These in turn can form the basis for determining the gas component or gas components, which in relation to the purge gas have changed concentration, and their origin.

In the measurement device according to FIG. 2, the pressure measurement, which serves the identification of the concentration changes from the pressure-time behaviour, is also considered in relation to the reference system, by switching the pressure sensor 10 as a differential pressure sensor between a sensor 1B of the measurement system and a sensor 1C of the reference system. In addition through the method described in DE 19925 842 A1 as referred to in the present description, absolute concentrations of the analysed gas components can occur through measurement and evaluation of the purge gas pressure using another pressure sensor 10 suitable for the measurement of the differential pressure.

For the analysis, e.g. of another gas component, a measurement system according to FIG. 1 or FIG. 2 can be complemented by further modules identical in construction with respective divergently configured sets of membranes, so that the measurements and evaluations take place for each set of membranes as described above.

For a version of the above described measurement method, which shall be called a passive measurement and which makes use of the dynamic instead of the thermodynamic equilibrium, a diffusion-supported purging of the pair of sensors 1AB takes place in step 1. For the passive measurement, the matrix 12 therefore serves as a purge gas, by using the spontaneously running diffusion processes for the purging after having exposed the pair of sensors 1AB to a reference state with air or to the matrix 12. The conditioning of the set of membranes thus takes place continuously in a diffusive manner, whereby the measurement chambers are permanently closed. Further procedural steps are to be realized as described above because the characteristic values, from which the gas components and its genesis are identified, are specific to gases as already stated above. Consequently, such non-stationary measurements can be used for the analysis of individual gases and genetic differentiation of gases.

FIG. 3 presents different timelines of the differential pressure $\Delta p_{sI}$ or $\Delta_{sII}$ and $\Delta p_r$; the former for a first gas component I and second gas component II, present as oxygen and carbon dioxide, each for various concentrations as parameter. It is evident that various concentrations of the relevant gas component I and II namely change the curve, but not the end points $t_{EI}$ and $t_{EII}$. It is also evident that the end points $t_{EI}$ and $t_{EII}$ of both gases differ sufficiently for a differentiation. In the presented method of analysis, the end points $t_{EI}$ and $t_{EII}$ are determined from the intersection of the respective timeline with the baseline 20. The latter presents, as mentioned above, the timeline of the reference differential pressure $\Delta p_r$, which is determined between both sensors of a reference system.

In FIG. 4, identified time differences $\Delta t = t_E - t_A$ are presented in the passive method via the concentration of the gas components, which by adding two different gases I and II, again oxygen and carbon dioxide, are realized as a matrix 12. For each of the gases I and II added from the outside, a mixture-matrix time $\Delta t_{mixI}$ and $\Delta t_{mixII}$ occurs as long as there is no additional reaction of the gas components with the matrix 12. Both values match the values of both gases calculated prior through simulation, and are independent from the concentration as shown for instance with gas II.

Deviating from these time differences, another value of the time difference $\Delta t = t_E - t_A$ occurs despite the gas components having been analysed in an identical manner if one part of the gas component, oxygen in the described example, in the matrix 12, in this case oxygen-enriched air, reacts with carbon dioxide. In this instance also, changes in concentration of the gas components oxygen and carbon dioxide can be noted. The in point 4 described evaluation however reveals that the determined divergent time difference $\Delta t = t_E - t_A$ demonstrates a divergent genesis (reaction) of the examined gas component. Through comparing $\Delta t$ with the values of $\Delta t_{OII}$ and $\Delta t_{mixII}$, which are known for the gases in question, the proportion of mixture and reaction (genetic composition) of the examined gas components is determined.

The invention claimed is:

1. Method for analysis of gas components of a gas composite matrix, with a pair of sensors, which each comprise a cavity enclosed by a membrane, wherein one side of each membrane is exposed to the matrix and another side of each membrane is exposed to a purge gas, for which initially, a baseline of a measuring system at a start point $t_A$ is defined, which is consistent with a diffusive state of equilibrium, and subsequently, a timeline of the differential pressure $\Delta p_s$ or differential volume from the start point $t_A$ is measured, which is created between both cavities as a consequence of permeation of the gas components of the matrix through both membranes, wherein both membranes of the sensors have different timelines for the permeation of said gas components, an end point $t_E$ is determined, at which the differential pressure or differential volume is consistent with the differential pressure or the differential volume measured at the start point $t_A$, and said permeating gas components are determined from the time difference $\Delta t = t_E - t_A$.

2. Method according to claim 1, wherein genesis of said gas components is determined by the time difference $\Delta t = t_E - t_A$.

3. Method according to claim 1, wherein a differential pressure $\Delta p_s$ in relation to a pair of reference sensors is identified by determining a differential pressure $\Delta p_{s1}$ of the pair of sensors and a differential pressure $\Delta p_r$ of the pair of reference sensors, whose membranes are exposed to the purge gas on both sides, and the differential pressure $\Delta p_s$ is determined by a difference between $\Delta p_{s1}$ and $\Delta p_r$.

4. Method according to claim 1, wherein a timeline of a reference differential pressure $\Delta p_r$, designated as baseline, is measured using a pair of reference sensors, whose membranes are exposed to the purge gas on both sides, and the end point $t_E$ is determined as an intersection of the timeline of the differential pressures $\Delta p_s$ with the baseline.

5. Method according to claim 1, further comprising a purging of the sensors via purge gas inlets and outlets to establish a dynamic diffusive equilibrium, and wherein the purge gas is a gas of a known composition.

6. Method according to claim 1, wherein a purging through the membrane takes place in a diffusive manner to establish a thermo-dynamic diffusive equilibrium, and wherein the purge gas is the gas of the matrix.

7. Method according to claim 1, wherein the differential volume $\Delta V$ is measured time-dependently, wherein the differential volume is created between both cavities of the pair of sensors or between a pair of reference sensors as a consequence of the permeation of the gas components of the matrix through both membranes.

8. Method according to claim 7, wherein concentration or change in concentration is quantitatively determined from a pressure-time curve of the differential pressure $\Delta p_s(t)$ or from a volume-time curve of the differential volume for the gas component that is determined qualitatively.

9. Device for the analysis of gas components of a gas composite matrix, comprising a first pair of sensors, which each comprise a cavity that is at least partly enclosed by a membrane, each membrane being exposed to the matrix on one side and to a purge gas in the cavity on another side, and at least one of a pressure measuring device for a time-dependent measurement of a differential pressure $\Delta p_s$, that is created between both cavities as a consequence of permeation of the gas components from the matrix and the purge gas through both membranes, or a volume measuring device for a time-dependent measurement of a differential volume, that is created between both cavities as a consequence of the permeation of the gas components from the matrix and the purge gas through the both membranes, wherein geometry and selectivity of the pair of sensors are coordinated so that the sensors exhibit different timelines of permeation for the gas components of the matrix, and a measurement system determining a time $t_E$ when the time-dependent measurement of differential pressure or of differential volume corresponds to a baseline at a start time $t_A$ representing a diffusive state of equilibrium and determining as components of matrix from the time difference $\Delta t = t_E - t_A$.

10. Device according to claim 9, wherein the sensors differ in their geometry to each other.

11. Device according to claim 9, wherein the membranes of the pair of sensors differ in their geometry to each other.

12. Device according to claim 9, wherein membranes of the pair of sensors differ in their material to each other.

13. Device according to claim 9, further comprising another pair of sensors identical in construction to each other, whose permeation characteristics deviate from those of the first pair of sensors.

14. Device according to claim 9, further comprising a pair of reference sensors identical in construction to each other, whose permeation characteristics are consistent with those of the first pair of sensors, and at least one of a pressure measuring device for a time-dependent measurement of a reference differential pressure $\Delta p_r$, that is created between both cavities of the pair of reference sensors during an analysis measurement, or a volume measurement device for a time-dependent measurement of a reference differential volume, that is created between both cavities of the pair of reference sensors during an analysis measurement.

15. Device according to claim 9, wherein the device contains a variety of pairs of sensors and reference sensors, each pair being coordinated in regard to permeation and geometrical characteristics.

\* \* \* \* \*